United States Patent
Sawada et al.

(10) Patent No.: US 8,388,893 B2
(45) Date of Patent: Mar. 5, 2013

(54) COMBINED DETECTOR

(75) Inventors: Kazuaki Sawada, Toyohashi (JP);
Junichi Matsuo, Toyohashi (JP);
Hirokazu Nakazawa, Toyoshashi (JP)

(73) Assignee: National University Corporation Toyohashi University of Technology, Toyohashi-shi, Aichi (JP)

( * ) Notice: Subject to any disclaimer, the term of this patent is extended or adjusted under 35 U.S.C. 154(b) by 233 days.

(21) Appl. No.: 12/809,558

(22) PCT Filed: Dec. 19, 2008

(86) PCT No.: PCT/JP2008/073261
§ 371 (c)(1),
(2), (4) Date: Jun. 18, 2010

(87) PCT Pub. No.: WO2009/081890
PCT Pub. Date: Jul. 2, 2009

(65) Prior Publication Data
US 2011/0236263 A1    Sep. 29, 2011

(30) Foreign Application Priority Data
Dec. 20, 2007 (JP) .................. 2007-329379

(51) Int. Cl.
*G01N 27/00* (2006.01)

(52) U.S. Cl. ...... 422/82.01; 422/52; 422/73; 422/82.05; 422/82.06; 422/82.07; 422/82.08; 422/82.09; 422/82.11; 422/407; 422/501; 422/502; 422/503; 422/504; 436/43; 436/63; 436/94; 436/149; 436/164; 436/172; 436/174; 436/177; 436/517; 436/518; 436/805; 436/809; 435/4; 435/7.1; 506/30; 250/214.1; 250/251; 250/576; 530/408; 714/752

(58) Field of Classification Search ............ 422/52, 422/73, 82.01, 82.05, 82.08, 82.09, 82.11, 422/99, 102, 407, 501, 502, 503, 504; 436/164, 436/177, 43, 63, 149, 172, 174, 518, 805, 436/809; 506/30; 435/29, 4, 6, 7.1; 250/214.1, 250/251, 576; 530/408; 714/752
See application file for complete search history.

(56) References Cited

U.S. PATENT DOCUMENTS
6,294,133 B1    9/2001    Sawada et al.

FOREIGN PATENT DOCUMENTS
| JP | H11-201775 | 7/1999 |
| JP | 2002-98667 | 5/2002 |
| JP | 2004028723 A * | 1/2004 |
| JP | 2008-28723 | 2/2008 |
| WO | 2006/095903 A1 | 9/2006 |

OTHER PUBLICATIONS

Lee et al, "High Performance Blood Glucose Sensor Using Charge Transfer Technique", Solid-State Sensors, Actuators and Microsystems Conference, 2007. Transducers 2007. International, Jun. 10-14, 2007, pp. 855-858.*

* cited by examiner

*Primary Examiner* — Dennis M White
(74) *Attorney, Agent, or Firm* — Quarles & Brady, LLP; Gavin J. Milczarek-Desai

(57) ABSTRACT

A combined detector capable of simultaneously detecting both a value indicating a physical/chemical phenomenon such as a pH value and the intensity of an energy beam such as light. The combined detector comprises a physical/chemical phenomenon detecting system (10) and an energy beam detecting system. The physical/chemical phenomenon detecting system (10) has a sensing section (21) whose potential varies with a physical/chemical phenomenon, a charge supply section (22) for supplying first charge to the sensing section, a charge supply control section (23) provided between the sensing section (21) and the charge supply section (22), a first charge storage section (26) for storing the first charge transferred from the sensing section (21), and a charge transfer control section (27) provided between the sensing section (21) and the first charge storage section (26). The sensing section (21) includes a semiconductor charge generating portion (15) for generating the first charge and second charge when receiving an energy beam such as light. The energy beam detecting system has the semiconductor charge generating portion (15) and a second charge storage section (31) adapted to store the second charge generated by the semiconductor charge generating portion (15) and having an opposite potential to the first charge storage section (26) with respect to the sensing section (21).

8 Claims, 5 Drawing Sheets

Source Follower

COMBINED DETECTOR

FIELD OF THE INVENTION

The present invention relates to a combined detector. The combined detector detects PH of the same object and light from the same object, for example.

BACKGROUND OF THE INVENTION

A single detector for detecting pH value of an object and light emitted from the object is proposed in patent document 1. The detector proposed in patent document 1 has a structure combined with a charge transfer type pH detector and a charge transfer type light detector to detect pH value and light alternately in time sequence. Namely, time of detecting pH value and time of detecting light are a little bit out of synchronization.

For attaining high S/N ratio, it is desirable to accumulate charge in the sensing section of the pH detector. If it is assumed to take 0.1 millisecond to accumulate charge one time, it takes 0.1 second to accumulate charge one hundred times, during which the sensing section is not secured to detect light.

If combined detectors are arranged like a matrix, pH distribution (pH image) and light distribution (light image) of the object can be detected.

The following patent documents 2 and 3 are also referred to as references for the invention.
Patent document 1: Japanese Patent Application Laid-Open (JP-A) No. 11-201775
Patent document 2: JP-A No. 2004-28723
Patent document 3: JP-A No. 2002-98667

DISCLOSURE OF THE INVENTION

Problems to be Solved by the Invention

When stirring microbe and fluid including blood etc. are detected, unless light distribution and pH distribution are detected simultaneously, the light distribution and the pH distribution are detected substantially in different areas. Thus, the difference between the light distribution and the pH distribution in time sequence hinders exact detection of moving object.

An object of the invention is to provide a combined detector for detecting physical and chemical phenomenon value and quantity of energy beam including light beam simultaneously.

Means for Solving the Problems

For attaining the object, inventors thought of the present invention by hard study. Namely, a first aspect of the present invention is defined as the following.

A combined detector comprising a chemical and physical phenomenon detecting system and an energy beam detecting system, the chemical and physical phenomenon detecting system comprising a first sensing section changed in potential depending on chemical and physical phenomenon, a first charge supply section for supplying a first charge to the first sensing section, a first charge supply control section formed between the first sensing section and the first charge supply section, a first charge storage section for storing the first charge transferred from the first sensing section, and a first charge transfer control section formed between the first sensing section and the first charge storage section, the first sensing section including a semiconductor charge generating section for generating the first charge and a second charge by receiving energy beam including light, and the energy beam detecting system comprising the semiconductor charge generating section, and a second charge storage section for storing the second charge generated in the semiconductor charge generating section and provided with opposite potential to the first charge storage section as compared with the first sensing section.

According to the first aspect of the combined detector, when the first charge is stored in the first charge storage section of the chemical and physical phenomenon detecting system, the second charge is stored independently in the second charge storage section of the energy beam detecting system. In other words, while the first charge corresponding to chemical and physical phenomenon value (for example, pH value) detected by the chemical and physical phenomenon detecting system is stored in the first charge storage section, the second charge corresponding to quantity (for example, intensity) of energy beam (for example, light) is stored simultaneously and continuously in the second charge storage section.

Therein, the first charge may be an electron or a hole. On the other hand, the second charge may be a hole or an electron. As defined in the second aspect of the present invention, in the chemical and physical phenomenon detecting system necessitating accumulated detections, an electron which enables a rapid transfer operation is preferred as the first charge. Accordingly, a hole is preferred for storage in the second charge storage section of the energy beam detecting system.

The third aspect of the present invention is defined as the following. Namely, in the combined detector according to the first aspect or the second aspect, a buried channel layer of opposite conductivity to conductivity of a semiconductor substrate is formed beneath a surface of the semiconductor substrate in the semiconductor charge generating section.

Therein, when a p-type semiconductor substrate is used, an n layer is disposed at least in the sensing section as the buried channel layer beneath the surface of the substrate. Since the buried channel layer is formed, a potential profile as shown in FIG. 1 is obtained.

Therein, an electron produced by photoelectric effect moves to a conduction band, and a hole moves to a valence band. Since an electron moves to a higher potential, the electron moves to a potential well. Reversely, a hole moves to a lower potential. A hole produced remotely from a surface (S) of the substrate runs away to the right direction (back surface of the substrate) shown in FIG. 1. On the other hand, a hole produced near to the surface (S) of the substrate (nearer to the surface (S) of the substrate than a valley (V) of potential) is stored in the top of potential. Such a hole can be read out as output of light.

As described above, a thickness of the buried channel layer (namely, depth of the layer doped with n-type dopant) is equal to or larger than a thickness into which the energy beam reaches.

The fourth aspect of the present invention is defined in the following. Namely, in the combined detector according to any one selected from the first aspect to the third aspect, the first charge supply section and the first charge storage section are formed at two opposed sides of the first sensing section, and the second charge storage section is formed at a remaining side of the first sensing section.

According to the combined detector defined above, since a versatile structure for a chemical and physical phenomenon detecting system is applied, fabrication process can be carried out easily.

The fifth aspect of the present invention is defined in the following.

Namely, in the combined detector according to any one selected from the first aspect to the third aspect, the first charge supply section and the first charge storage section are formed at two adjacent sides of the first sensing section, and the second charge storage section is formed at remaining adjacent sides of the first sensing section.

According to the combined detector defined above, the second charge storage section is formed at the remaining adjacent sides. The second charge storage section formed at the remaining adjacent sides may have a continuous body. So, the second charge storage section secures a larger total volume to realize wider dynamic range for detection of energy beam.

The sixth aspect of the present invention is defined in the following.

Namely, in the combined detector according to any one selected from the first aspect to the fifth aspect, the second charge storage section is provided with an output gate disposed via an insulating film and further includes means for reading out first charge produced in the output gate by capacitance coupling corresponding to the second charge stored in the second charge storage section.

The first charge (corresponding to the second charge stored in the second charge storage section) read out above is converted into voltage for output via a source-follower circuit with a simple structure, for example. Namely, according to the sixth aspect of the combined detector, a quantity of the energy beam can be detected based on quantity of the second charge stored in the second charge storage section.

The seventh aspect of the present invention is defined in the following.

Namely, in the combined detector according to any one selected from the first aspect to the fifth aspect, there provided with a second sensing section changed in potential depending on potential of the second charge storage section, a second charge supply section for supplying the first charge or the second charge to the second sensing section, a second charge supply control section formed between the second sensing section and the second charge supply section, a third charge storage section for storing the first charge or the second charge transferred from the second sensing section, and a second charge transfer control section formed between the second sensing section and the third charge storage section, wherein timing of supplying a charge from the second charge supply section to the second sensing section is synchronized with timing of supplying a charge from the first charge supply section to the first sensing section, and timing of transferring a charge from the second sensing section to the third charge storage section is synchronized with timing of transferring a charge from the first sensing section to the first charge storage section.

According to the seventh aspect of the present invention, since potential of the second charge storage section (depending on the second charge stored therein) is detected by a charge transfer type potential sensor, quantity of the charge stored in the second charge storage section is detected exactly.

Then, since the charge transfer type potential sensor is provided with the same structure as, or similar structure to that of the chemical and physical phenomenon detecting system, fabrication process thereof can be carried out easily.

Further, synchronized with both the operation timings, the seventh aspect of the combined detector can be controlled easily.

Figure 1:
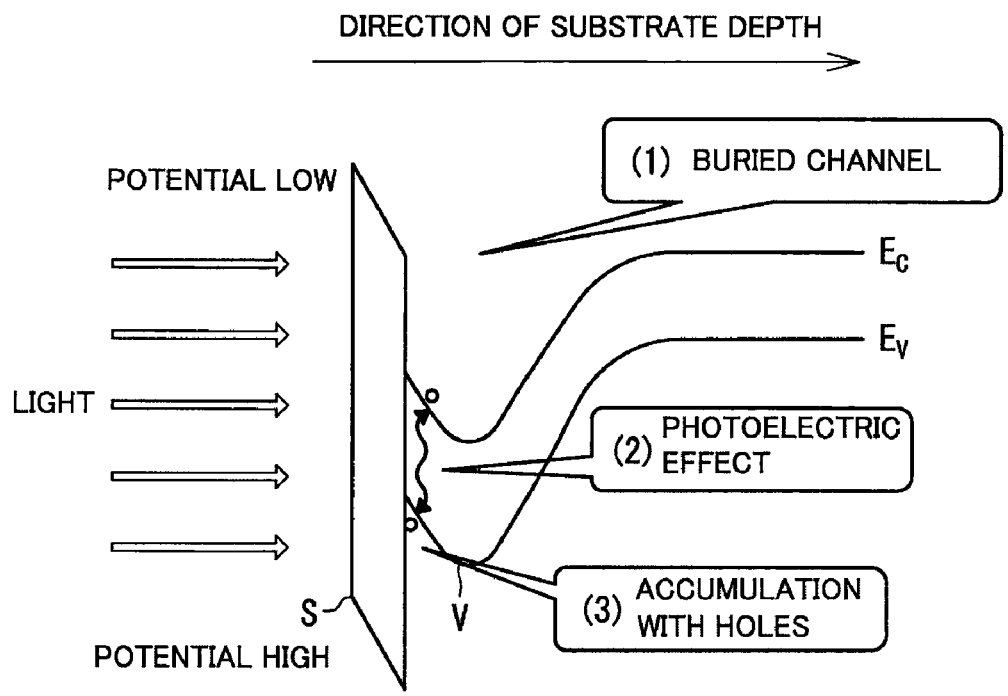
FIG. 1 is a view explaining movement of holes in a sensing section.

DESCRIPTION OF THE REFERENCE NUMERALS 1, 200, 300 Combined detector
11 Semiconductor substrate
13 Insulating film
10 pH detecting system
21 Sensing section
22 Charge supply section
23 Charge supply control section
26 First charge storage section
27 Charge transfer control section
31 Second charge storage section

EMBODIMENTS

Figure 2:
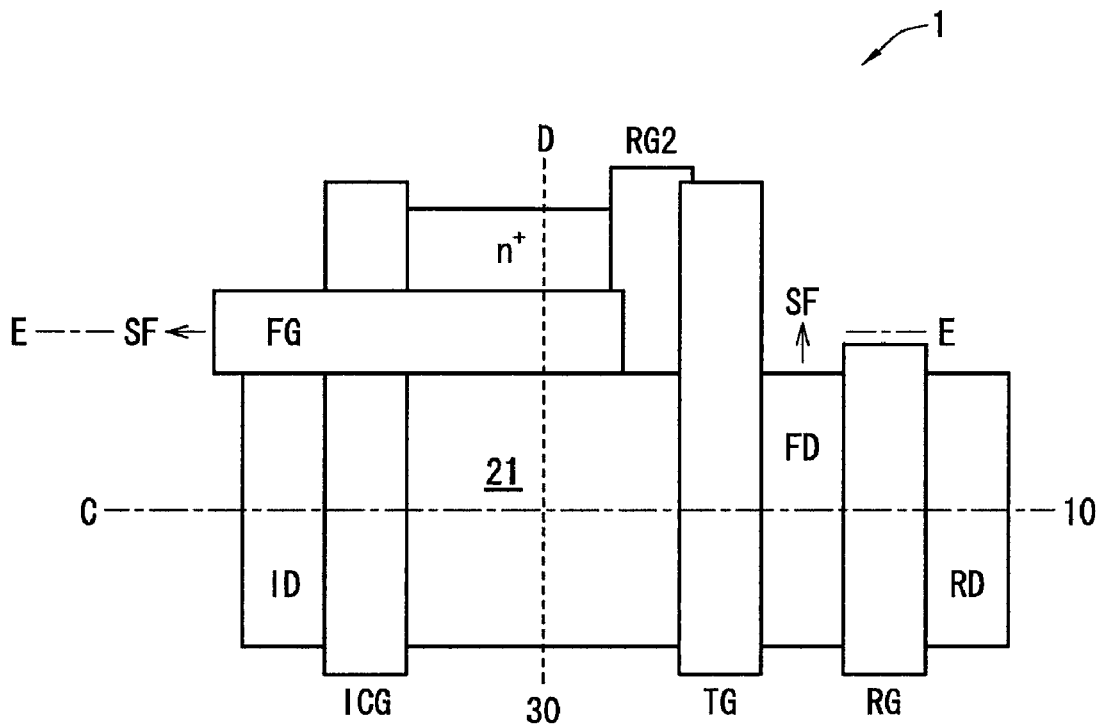
FIG. 2 is a plan view of a combined detector of one embodiment.

FIG. 2 shows a plan view of a combined detector 1 of an embodiment of the present invention. A sectional view taken on line C and a sectional view taken on line D in FIG. 2 are shown in FIG. 3A. A sectional view taken on line E is shown in FIG. 4.

The combined detector 1 shown in FIG. 2 comprises a pH detecting system 10 and a light detecting system 30.

The pH detecting system 10 is formed along the C-line. The structure of such the pH detecting system 10 is similar to that of a conventional pH detecting system. Namely, as shown in FIG. 3A, an n layer and an n+ layer are formed on the surface of a (p type) silicon substrate 11. On the surface of the silicon substrate 11, a silicon oxide film (insulating film) 13 is formed. On such the insulating film 13, a metal film is patterned to form various kinds of electrodes. The n layer corresponds to a buried channel layer 15.

In FIG. 3A, numeral 21 indicates a sensing section, numeral 22 indicates a charge supply section, and numeral 23 indicates a charge supply control section.

In the sensing section 21, on the surface of the insulating film 13, a concave portion is formed to contact a detected object on wet condition, with a reference electrode 25 disposed. In the sensing section 21, beneath the surface of the substrate 11, the buried channel layer (n layer) is formed.

When such the sensing section 21 contacts the detected object, potential varies with pH of the detected object. In addition, when light is incident on the sensing section 21, electrons and holes are generated by photoelectric effect. Herein, as the buried channel layer is formed in the sensing section 21, a portion of the holes are accumulated to the top of the potential beneath the surface of the substrate, as described above (as referred to FIG. 1). On the other hand, the electrons enter into a potential well formed according to pH.

The charge supply section 22 provided with an n+ region is connected to an input diode ID. A charge supply control section 23 is disposed between the sensing section 21 and the charge supply section 22. In the charge supply control section 23, the semiconductor substrate 11 is faced with an input control gate electrode ICG through the insulating film 13. A predetermined voltage is applied to the gate electrode ICG to form a potential wall between the charge supply section 22 and the sensing section 21.

A second input control gate electrode ICG controllable independently may be formed between the sensing section 21 and the input control gate electrode ICG. In the sensing section 21, a continuous potential well may be formed by the second input control gate, to absorb electrons remaining in the sensing section 21 into the continuous potential well.

In FIG. 3A, numeral 26 indicates the first charge storage section, and numeral 27 indicates a charge transfer control section 27. The first charge storage section 26 is also referred to as a floating diffusion region and provided with an n+ region of the substrate 11.

The charge transfer control section 27 is disposed between the sensing section 21 and the first charge storage section 26. In the charge transfer control section 27, the semiconductor substrate 11 is faced with a transfer gate electrode TG through the insulating film 13. A predetermined voltage is applied to the transfer gate electrode TG to form a potential wall between the sensing section 21 and the first charge storage section 26. Then, by change of the height of the potential wall, the charges in the sensing section 21 are transferred to the first charge storage section 26.

Figure 5:
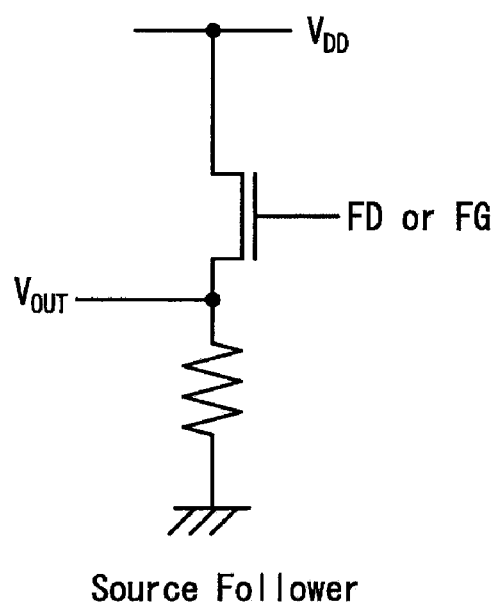
FIG. 5 shows a structure of a source-follower circuit converting detected result of the combined detector into output voltage.

Electrons stored in the first charge storage section 26 are read out via a source-follower circuit shown in FIG. 5 at a predetermined timing and converted into output voltage Vout. Namely, as the gate voltage of a MOS transistor changes according to the charges stored in the first charge storage section 26, current flowing through a resistor changes. As a result, the output voltage Vout also changes.

A reset gate electrode RG and a reset diode are used for resetting the charges of the first charge storage section 26.

In FIG. 2, the light detecting system 30 is formed along line D.

Numeral 31 shown in FIG. 3A indicates the second charge storage section. In view of potential of the sensing section 21, potential of the second charge storage section 31 is opposite to that of the first charge storage section 26. Therefore, among holes produced beneath the surface of the sensing section 21 by photoelectric effect, holes near to the second charge storage section 31 are stored in the second charge storage section 31 (as referred to FIG. 1).

In the second charge storage section 31, the semiconductor substrate 11 is faced with a floating gate electrode FG via the insulating film 13.

Numeral 33 indicates an n+ region.

The sectional view taken on line E in FIG. 2 is shown in FIG. 4.

As shown in FIG. 4, the second charge storage section 31 is disposed between an input control gate electrode ICG with comparatively high potential and a reset gate electrode RG2. By potential wells 36 and 37 produced by these electrodes and a potential well produced by the n+ region 33, the second charge storage section 31 is independent of other regions. In other words, holes can be stored in anytime.

The floating gate electrode FG is opposed via the insulating film (thin film) 13 to the surface of the semiconductor substrate which stores holes. In the floating gate electrode FG, electrons are produced by capacitance coupling. These electrons are read out by the source-follower circuit shown in FIG. 5 and converted into the output voltage Vout. Namely, as the gate voltage of a MOS transistor varies with the charges stored in the floating gate electrode FG, current flowing through the resistor changes. As a result, output voltage Vout also changes.

Figure 3:
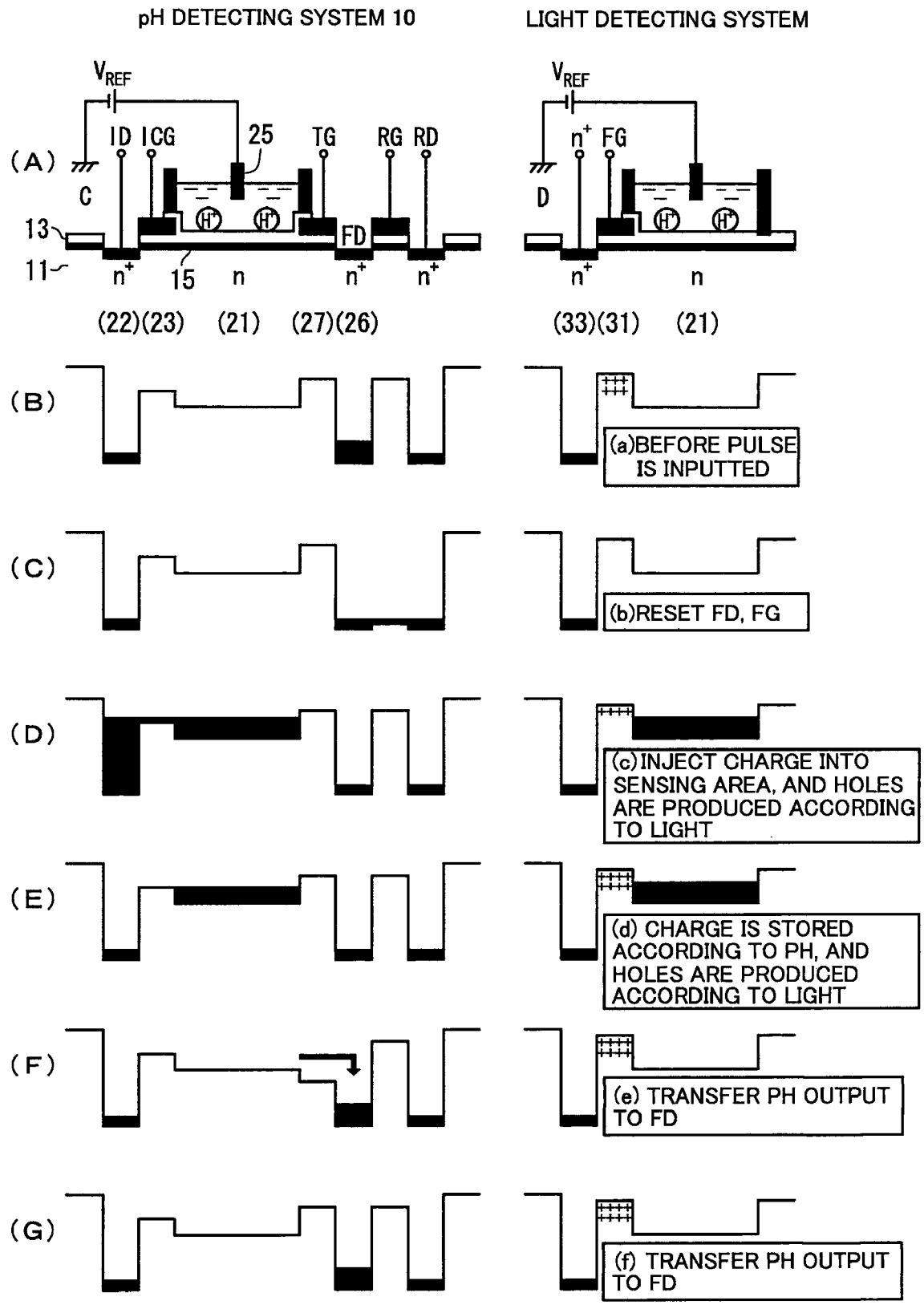
FIG. 3 is a view explaining a structure and operation of the combined detector shown in FIG. 2.
Figure 4:
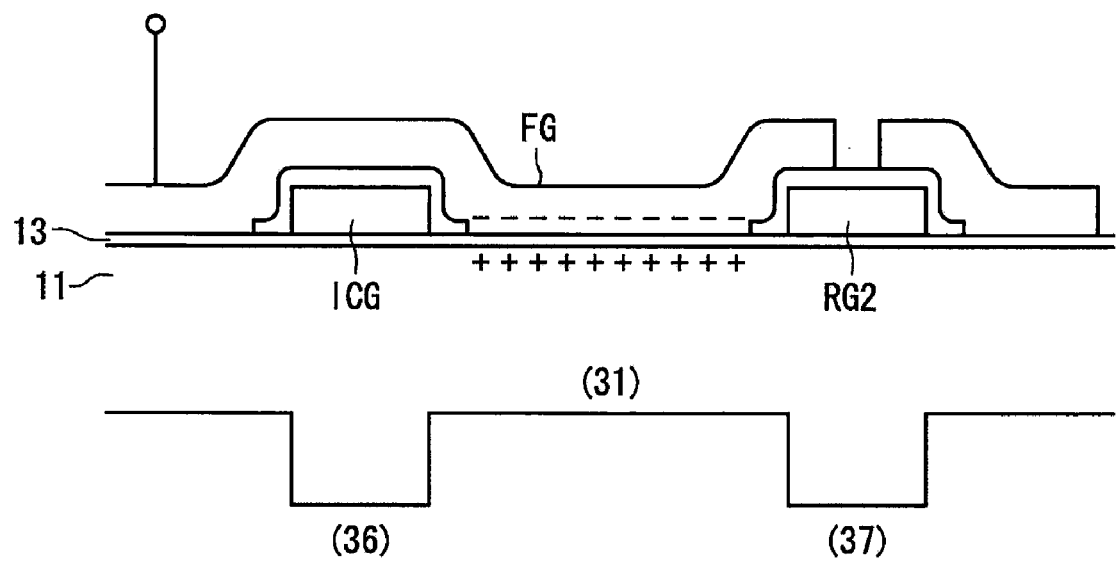
FIG. 4 shows a cross sectional structure taken on line E-E in FIG. 2.

Next, operation of the combined detector of the embodiment is explained (with reference to FIG. 3).

In FIG. 3B, as a result of the previous detection, electrons remains in the first charge storage section 26, and holes are stored in the second charge storage section 31.

Following such a state, each of charges stored in the first charge storage section 26 and charges stored in the floating gate electrode FG is read out by each of the source-follower circuits connected to each of the first charge storage section and the first charge storage section to obtain each of output voltage Vout.

Then, as shown in FIG. 3C, the potential of the reset gate electrode RG is controlled to discharge the charges stored in the first charge storage section 26 from the reset diode RD to the outside. On the other hand, as to the holes stored in the second charge storage section, the potential of the second reset gate electrode RG2 is controlled to extinguish the potential well 37. Therefore, the holes diffuse beneath the surface of the substrate and disappear.

As a result, the combined detector 1 is reset.

In FIG. 3D, operation of detecting new pH value and light is resumed.

In FIG. 3D, electrons overflow the charge supply section 22 to fill the sensing section 21 with electrons. Next, as shown in FIG. 3E, when electrons are reduced in the charge supply section 22, electrons in the sensing section 21 are separated from by the potential wall of the charge supply control section 23, so that a quantity of electrons corresponding to the depth of the potential (which is dependent on pH) remain in the sensing section 21.

In FIG. 3F, the potential of the transfer gate electrode TG is controlled to transfer electrons remaining in the sensing section 21 to the first charge storage section 26 which stores the electrons.

Repeating operations shown in FIGS. 3D-3F, electrons are accumulated in the first charge storage section.

During time (for repeating the operations shown in FIGS. 3D-3F), holes produced by light incident on the sensing section 21 are stored continuously in the second charge storage section 31. The quantity of holes produced is proportional to the quantity of light incident on. Namely, when a pH value is detected, the quantity of light incident on the sensing section is detected simultaneously.

Figure 6:
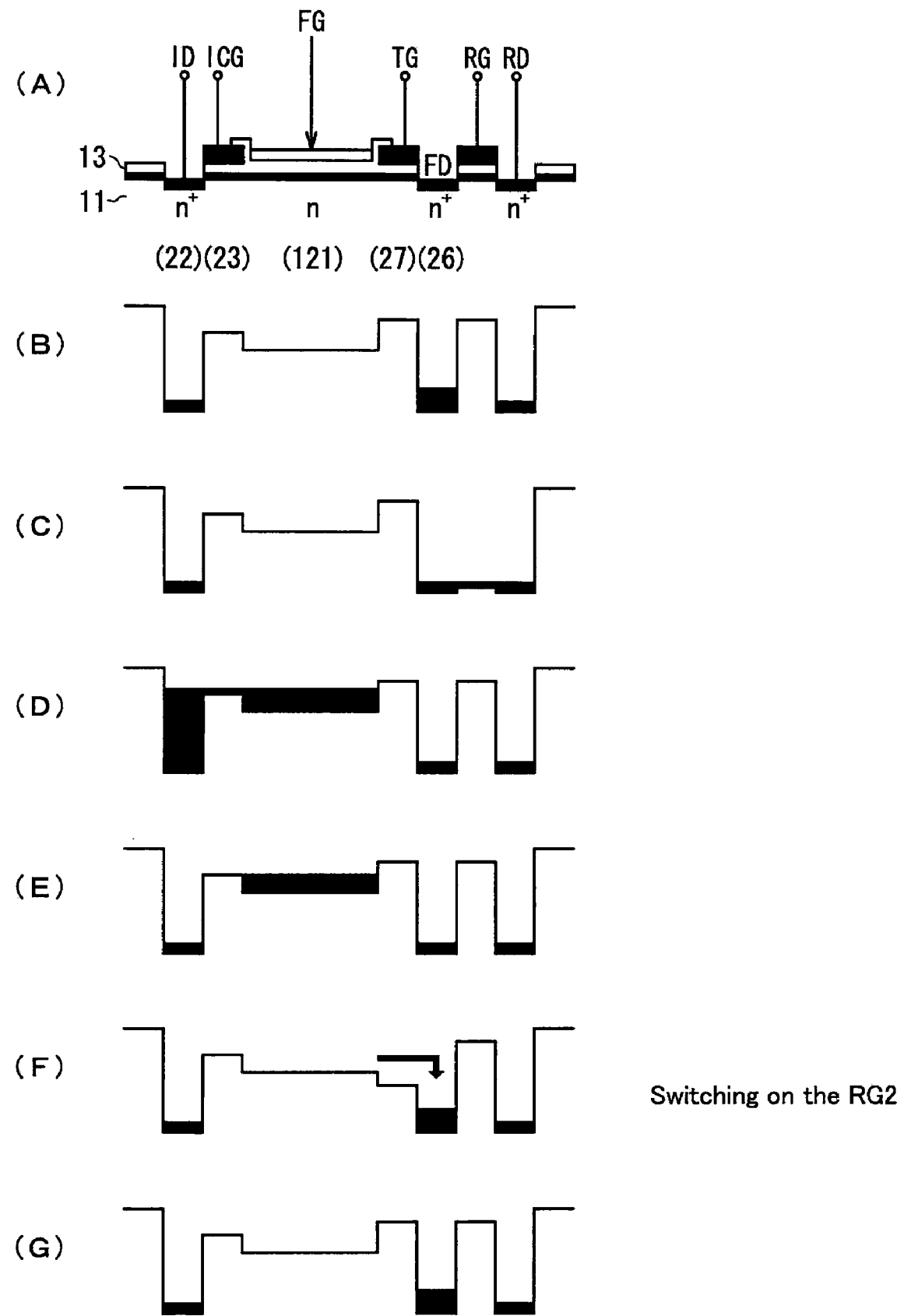
FIG. 6 shows another output converting means of detected result of the combined detector.

In such a state, if each of charges stored in the first charge storage section 26 and charges stored in the floating gate electrode FG is read out by each of the source-follower circuits connected to each of the first charge storage section 26 and the floating gate electrode FG, output voltage Vout corresponding to pH value and output voltage Vout corresponding to the quantity of light incident on the sensing section during the pH value detection are obtained simultaneously FIG. 6 shows another system which detects a charge in the floating gate electrode FG. In FIG. 6, the same element as that of FIG. 2 is referred to with the same reference numeral of FIG. 2 and the description thereof is eliminated. In FIG. 6, numeral 121 indicates a charge detecting section.

In this example, the quantity of the charge stored in the floating gate electrode FG is detected by a versatile physical and chemical phenomenon detecting device. In such a versatile physical/chemical phenomenon detecting device, a kind of structure similar to that of the pH detecting system 10 of the embodiment is provided. Thereby, the manufacturing process is utilized in common to reduce manufacturing cost.

In the detecting device of FIG. 6, it is desirable to synchronize timing of supplying charges and timing of transferring the charges with timings thereof in the combined detector 1 shown in FIG. 2. Further, it is desirable to reset once holes stored in the second charge storage section 31 by switching on the second reset gate electrode RG2 at timing of transferring the charges (as referred to FIG. 6F). Therefore, it is made possible to synchronize operation of detecting pH value with operation of detecting light more precisely.

Figure 7:
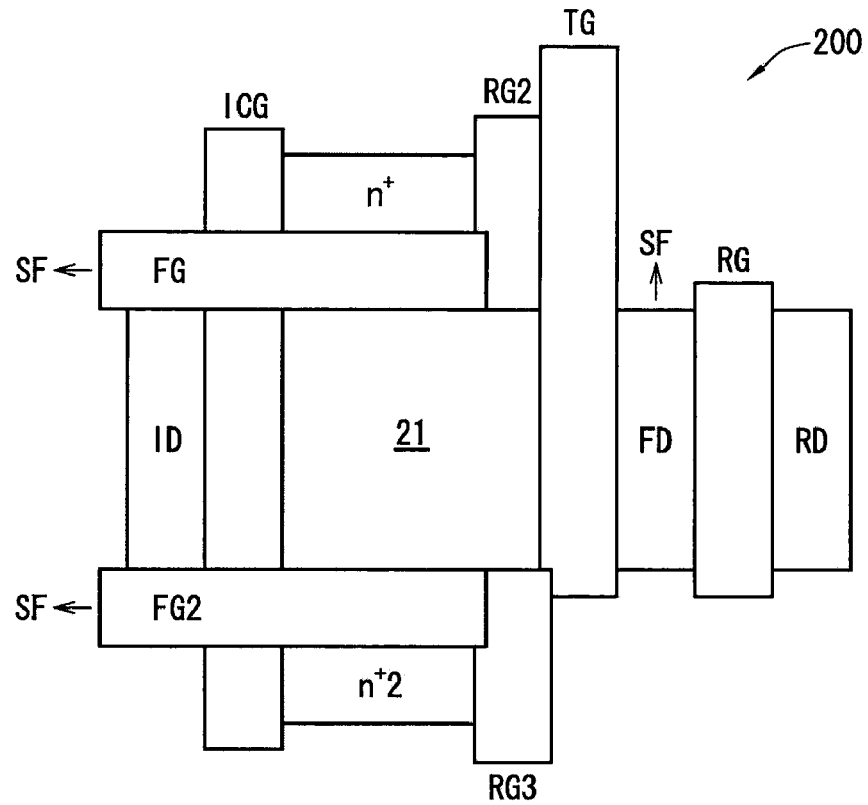
FIG. 7 is a plan view of a combined detector of another embodiment.

FIG. 7 shows a combined detector of another embodiment 200. In FIG. 7, the same element as that of FIG. 2 is referred to with the same reference numeral of FIG. 2 and the description thereof is eliminated.

In the combined detector 1 shown in FIG. 2, as to the sensing section 21 of the shape of a rectangle, the charge supply section and the charge supply control section are disposed at the one side of the opposed sides of the rectangle, and the first charge storage section and the charge transfer control section are disposed at the other side of the opposed sides of the rectangle, and the second charge storage section is disposed at another side of the rectangle.

In the embodiment shown in FIG. 7, the second charge storage sections are disposed at the two sides of the opposed sides of the rectangle. Namely, as compared with FIG. 2, the second floating gate electrode FG2, the third reset gate electrode RG3, and the second n+ region are formed along the lower side of the sensing section 21.

The second floating gate electrode FG2 is connected with the source-follower circuit shown in FIG. 5 or the detecting device shown in FIG. 6.

Figure 8:
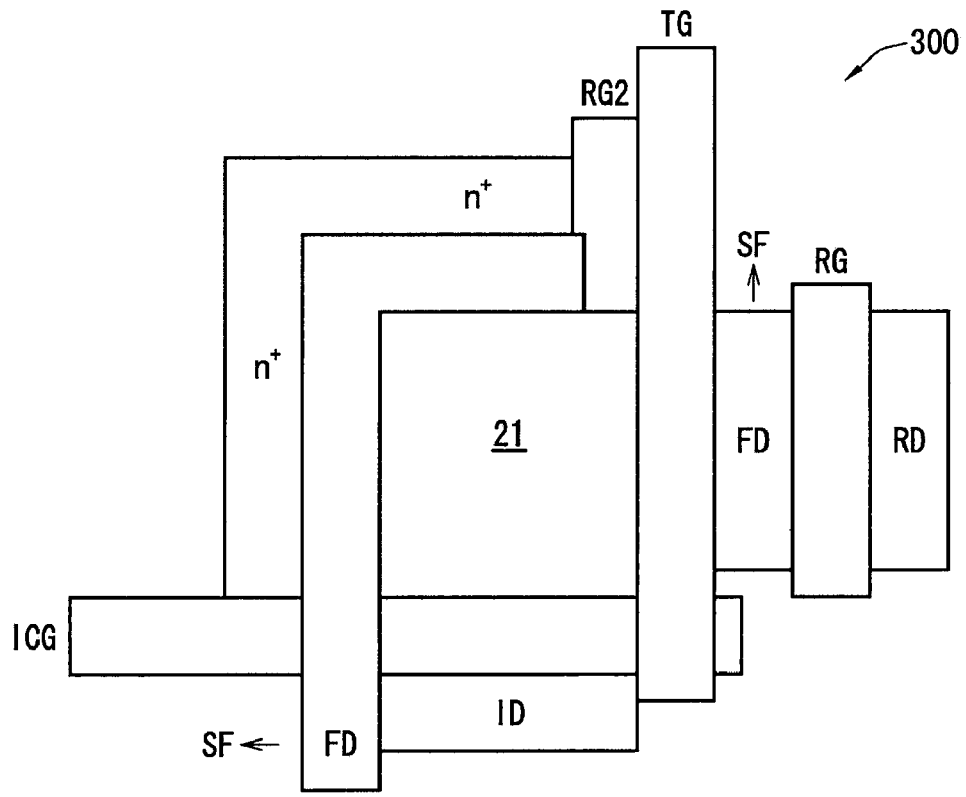
FIG. 8 is a plan view of a combined detector of another embodiment.

FIG. 8 shows a combined detector of another embodiment 300. In FIG. 8, the same element as that of FIG. 2 is referred to with the same reference numeral of FIG. 2 and the description thereof is eliminated.

In the embodiment shown in FIG. 8, as to the sensing section 21 of the shape of a rectangle, the charge supply section and the charge supply control section are disposed at the one side of adjacent sides of the sensing section, and the first charge storage section and the charge transfer control section are disposed at the other side of the adjacent sides of the sensing section, and the second charge storage section is disposed at the remaining two sides of the sensing section 21.

According to such a structure, the second charge storage section secures a larger total volume to store more holes, which realizes wider dynamic range. In the embodiment shown in FIG. 8, as one integrated floating gate is provided in the combined detector, the structure of the combined detector is more simplified to make the combined detector small, as compared with the embodiment shown in FIG. 7.

In each of the combined detectors of the embodiments explained above, it is desired to dispose electrodes and high density doped regions in the periphery of the sensing section and rectilinearly from the sensing section. Accordingly, the combined detectors of the present invention are suitable for an integrated array to enable to image precisely each distribution of pH value and quantity of light of the object detected at the same time.

The present invention is not limited to the illustrated embodiments or examples alone, but may be changed or modified within the scope easily devised by those skilled in the art without departing from the spirit of the present invention.

What is claimed is:

1. A combined detector comprising a chemical and physical phenomenon detecting system and an energy beam detecting system:
    said chemical and physical phenomenon detecting system comprising
    a first sensing section changed in potential depending on chemical and physical phenomenon,
    a first charge supply section configured to supply a first charge to said first sensing section,
    a first charge supply control section formed between said first sensing section and said first charge supply section,
    a first charge storage section configured to store said first charge transferred from said first sensing section, and
    a first charge transfer control section formed between said first sensing section and said first charge storage section,
    said first sensing section including a semiconductor charge generating section configured to generate an additional charge of the same polarity as said first charge and a second charge having opposite polarity to said first charge by receiving an energy beam including light, and
    said energy beam detecting system comprising
    said semiconductor charge generating section, and
    a second charge storage section configured to store said second charge generated in said semiconductor charge generating section and provided with opposite potential to said first charge storage section.

2. The combined detector according to claim 1, wherein said first charge is an electron and said second charge is a hole.

3. The combined detector according to claim 1, wherein a buried channel layer of opposite conductivity to conductivity of a semiconductor substrate is formed beneath a surface of said semiconductor substrate in said semiconductor charge generating section.

4. The combined detector according to claim 1, wherein said first charge supply section and said first charge storage section are formed at two opposed sides of said first sensing section, and said second charge storage section is formed at a remaining side of said first sensing section.

5. The combined detector according to claim 1, wherein said first charge supply section and said first charge storage section are formed at two adjacent sides of said first sensing section, and said second charge storage section is formed at remaining sides of said first sensing section.

6. The combined detector according to claim 1, wherein said second charge storage section is provided with an output gate disposed via an insulating film and further includes means for reading out a first charge produced in said output gate by capacitance coupling corresponding to said second charge stored in said second charge storage section.

7. The combined detector according to claim 1, comprising:
    a second sensing section changed in potential depending on potential of said second charge storage section,
    a second charge supply section for supplying said first charge or said second charge to said second sensing section,
    a second charge supply control section formed between said second sensing section and said second charge supply section, a third charge storage section for storing said first charge or said second charge transferred from said second sensing section, and a second charge transfer control section formed between said second sensing section and said third charge storage section, wherein timing of supplying a charge from said second charge supply section to said second sensing section is synchronized with timing of supplying a charge from said first charge supply section to said first sensing section, and timing of transferring a charge from said second sensing section to said third charge storage section is synchronized with timing of transferring a charge from said first sensing section to said first charge storage section.

8. The combined detector according to claim 1, wherein said semiconductor charge generating section is doped with a first conductivity type impurity material, said energy beam detecting system comprises a reset gate electrode and a well region doped with said first conductivity type impurity material, and said second charge storage section is surrounded by said semiconductor charge generating section, said reset gate electrode, said well region and said first charge supply control section, and is provided with opposite potential to said first charge storage section as compared with said first sensing section.

* * * * *

UNITED STATES PATENT AND TRADEMARK OFFICE
CERTIFICATE OF CORRECTION

PATENT NO.        : 8,388,893 B2
APPLICATION NO.   : 12/809558
DATED             : March 5, 2013
INVENTOR(S)       : Sawada et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 232 days.

Signed and Sealed this
First Day of September, 2015

Michelle K. Lee
*Director of the United States Patent and Trademark Office*